(12) United States Patent
Wolff et al.

(10) Patent No.: US 6,740,066 B2
(45) Date of Patent: May 25, 2004

(54) URINE COLLECTION DEVICE

(75) Inventors: Heinz Siegfried Wolff, London (GB); Felicity Ann Jowitt, Sunbury on Thames (GB); Eleanor Ann Tinnion, Slough (GB)

(73) Assignee: Brunel University (GB)

( * ) Notice: Subject to any disclaimer, the term of this patent is extended or adjusted under 35 U.S.C. 154(b) by 6 days.

(21) Appl. No.: 09/963,995

(22) Filed: Sep. 26, 2001

(65) Prior Publication Data
US 2002/0087131 A1 Jul. 4, 2002

Related U.S. Application Data (63) Continuation of application No. PCT/GB00/01165, filed on Mar. 27, 2000.

(30) Foreign Application Priority Data
Mar. 26, 1999 (GB) .............................................. 9906888

(51) Int. Cl.[7] .............................. A61M 1/00; A61F 5/44
(52) U.S. Cl. ...................... 604/319; 604/323; 604/347; 604/355; 604/544
(58) Field of Search ................................ 604/317–327, 604/329, 344, 346, 347, 349, 350, 351, 355

(56) References Cited

U.S. PATENT DOCUMENTS

| 3,575,158 A | * | 4/1971 | Summers ..................... 600/30 |
|---|---|---|---|
| 4,345,342 A | | 8/1982 | Saito |
| 4,631,061 A | | 12/1986 | Martin |
| 4,955,391 A | * | 9/1990 | Parker et al. ................ 600/584 |
| 5,002,541 A | | 3/1991 | Conkling et al. |
| 5,195,997 A | | 3/1993 | Carns |
| 5,466,229 A | * | 11/1995 | Elson et al. ................. 604/317 |
| 5,678,564 A | * | 10/1997 | Lawrence et al. ........... 600/574 |
| 5,681,297 A | * | 10/1997 | Hashimoto et al. ......... 604/355 |
| 5,741,238 A | * | 4/1998 | Bradbury et al. ............ 604/322 |
| 5,776,118 A | * | 7/1998 | Seifert et al. ................ 604/317 |
| 5,911,222 A | * | 6/1999 | Lawrence et al. ........... 600/574 |
| 6,007,524 A | * | 12/1999 | Schneider .................... 604/327 |
| 6,027,490 A | * | 2/2000 | Radford et al. .............. 604/540 |
| 6,372,182 B1 | * | 4/2002 | Mauro et al. .................. 422/56 |
| 6,394,988 B1 | * | 5/2002 | Hashimoto .................. 604/355 |
| 6,443,939 B1 | * | 9/2002 | Oki et al. .................... 604/393 |
| 6,488,675 B1 | * | 12/2002 | Radford et al. .............. 604/540 |
| 2002/0010446 A1 | * | 1/2002 | Maimets ...................... 604/355 |

* cited by examiner

Primary Examiner—Weilun Lo
Assistant Examiner—Michael Bogart
(74) Attorney, Agent, or Firm—Craig A. Fieschko, Esq.; DeWitt Ross & Stevens S.C.

(57) ABSTRACT

A device for collecting urine includes a container kept at vacuum, an interface locatable at the urethral opening of a person and a pump operable to create a vacuum within the container. A sensor senses the presence of urine at the interface and opens a valve to allow the pumping of urine from the interface to the container.

18 Claims, 11 Drawing Sheets

URINE COLLECTION DEVICE

CROSS-REFERENCE TO RELATED APPLICATIONS

This application is a continuation of International (PCT) Patent Application PCT/GB00/01165 filed Mar. 27, 2000 (designating the United States of America), which in turn claims priority to British Patent Application 9906888.4 filed Mar. 26, 1999, both of which are incorporated by reference herein.

FIELD OF THE INVENTION

This disclosure concerns an invention relating generally to a urine collection device for users with urinary incontinence.

BACKGROUND OF THE INVENTION

The present invention relates to a urine collection device, the preferred embodiment using a stored vacuum to allow immediate rapid removal of urine at the rate it is produced.

Millions of people worldwide are afflicted with the problem of urinary incontinence. The economic costs of this distressing condition are extremely high but the cost in terms of human suffering is incalculable. Both men and women are afflicted by the condition although many more women are affected and incidence increases with age.

For many younger men external catheter systems provide an adequate solution to the problem of severe urinary incontinence, but these systems are far less satisfactory for older men who are more likely to experience continence problems. For women incontinence management solutions are extremely limited. Internal catheters are associated with a host of medical problems, particularly urinary tract infections and urethral erosions. Large disposable pads to absorb urine are a safer option but are far from an ideal solution. Pads are bulky and require frequent changing if the wearer is to remain comfortable and free from odor problems. For immobile patients and those with sensory loss, wet pads can exacerbate the risk of pressure injury.

One of the major problems in designing a device to cope with incontinence is the very high flow rate which is a characteristic of urine flow. During a void the urine flow rate increases rapidly to a peak rate of 25–30 milliliters per second. To pump urine directly requires a powerful pump able to reach a high flow rate as soon as it is activated. This is extremely difficult to achieve and would require a much larger pump and power source than can be easily transported.

SUMMARY OF THE INVENTION

The invention involves a urine collection device which is intended to at least partially solve the aforementioned problems. To give the reader a basic understanding of some of the advantageous features of the invention, following is a brief summary of preferred versions of the device. As this is merely a summary, it should be understood that more details regarding the preferred versions may be found in the Detailed Description set forth elsewhere in this document. The claims set forth at the end of this document then define the various versions of the invention in which exclusive rights are secured.

The preferred embodiment of the urine collection device is useful for individuals who are unable to control the flow of urine or who are not technically incontinent but whose limited mobility makes transfer to the toilet extremely difficult. The preferred embodiment is designed to remove urine at the rate at which it is produced either from an interface positioned in the patient's underwear or from a portable urinal. The device uses a vacuum reservoir, maintained in a rigid storage container, to produce a strong suction at the moment the device is activated.

Further advantages, features, and objects of the invention will be apparent from the following detailed description of the invention in conjunction with the associated drawings.

BRIEF DESCRIPTION OF THE DRAWINGS

FIG. 2b is a enlarged cross-sectional view of the top of the large capacity device of FIG. 2a;

FIG. 3b is a cross-sectional view of the small capacity device of FIG. 3a;

FIG. 3c is an enlarged cross-sectional view of the top of the small capacity device of FIG. 3a;

FIG. 5b is a cross-sectional view of the layered female interface of FIG. 5a.

DETAILED DESCRIPTION OF PREFERRED EMBODIMENTS OF THE INVENTION

Two basic preferred versions of the device are described below, which can be triggered by two different methods. The first described version is designed for individuals who are in wheelchairs and incorporates a very large capacity storage container which could contain as much urine as would be produced in a twelve hour period. The second described version is designed for individuals who are mobile and self-sufficient and has a small container which would need to be emptied after each operation. The devices comprise four main parts:

(1) A rigid container which is connected by a tube to a small pump and pressure switch or vacuum transducer and switch. The pump evacuates air from the container until it reaches a set vacuum at which the pressure switch or vacuum transducer and switch, turns off the pump. The pressure switch, or vacuum and transducer and switch, is set so that every time the vacuum falls slightly below the set vacuum, the pump will activate again. By this means a vacuum is maintained in the container. There is a hydrophobic filter between the pump and the urine storage container to prevent liquid from being pumped out of the container. The pump may, for example, be a diaphragm or piston pump or any other suitable pump.

(2) The interface tube from the interface to the container and valve. The interface is connected to the container by a long flexible tube. The valve acts on the tube close to the container. The valve is normally closed, and holds the stored vacuum in the container. The interface with the patient can either be in the form of a pad positioned in the patient's underwear or a portable urinal. The valve may, for example, be a solenoid valve or any other suitable valve.

(3) The lid of the container, which incorporates a high bubble-point filter. The tube from the interface is connected into the top of the lid. The high bubble-point filter, when wetted, will only allow liquid to pass through it. The filter also has a bypass to allow the air in the tube to be evacuated before the oncoming urine.

(4) The trigger, pressure transducer and control electronics. The trigger, for the valve to open, can either be a remote manual operation or via an electronic sensor which is positioned in the interface. The electronic sensor detects the presence of urine and triggers the device to operate without any other intervention. This trigger sends a signal to the control electronics to open the valve. When urine production stops, either the pressure transducer senses that the pressure has fallen significantly in the container and it sends a signal to the control electronics to close the valve, or the valve is closed by the a signal from the sensor in the pad because the presence of urine is no longer being sensed. The valve can be triggered to close in several different ways, for example: 1) when the sensor in the interface no longer detects the presence of urine; 2) when the fall in vacuum within the storage container at the end of urine production is sensed by the pressure transducer which can trigger the valve to close; and/or 3) the valve could be set to close in response to a time switch.

To prepare the device for use the pump evacuates the container to about 0.5 to 0.7 bar absolute. When the desired vacuum is reached the pressure switch deactivates the pump and the vacuum is maintained within the container. When the device is triggered, the valve opens, releasing the vacuum from the container. The vacuum sucks urine along the tube from the interface. As the vacuum falls in the container, the pump is switched on to maintain the vacuum. If there is a mixed stream of air and urine passing into the device, the vacuum is maintained because the high bubble-point filter only allows urine to pass through it. When urine production stops, there is a short delay before the valve closes so that any residual urine is sucked out of the pad and tube. The pump remains active until the vacuum is restored so that the device is ready for the next occurrence.

The large capacity devices of FIGS. 1a, 1b, 1c, and 2a, 2b preferably have a 1.5–2.5 liter capacity rigid storage container 1. The lid to the container has a bag 2 attached to it which lines the inside of the container. The liner and lid are disposable to avoid contaminating the storage container with urine. In the wall of this liner there are one or more hydrophobic filters 3 with pore size small enough to prevent the passage of bacteria. The surface area of the filter is sufficient to allow an air flow through it to keep pace with the maximum urine influx, but will not allow any urine to pass through. The purpose of the filter is to allow the volume inside the liner to be evacuated, and to remove any air sucked into the container with the urine. The filter also prevents any bacteria escaping from the urine storage liner into the pump or the surrounding atmosphere.

The volume within the container is connected to the small diaphragm pump 4, via an outlet 20. The pump should have a flow rate of at least 2 liters of air per minute at atmospheric pressure. The pump outlet can have a silencer 41 fitted to reduce noise. The diaphragm pump is controlled by a pressure switch or pressure transducer and switch 5. The pressure switch or pressure transducer and switch, activates the pump whenever the vacuum is less than a predetermined pressure, for example, less than 0.7 bar, and disconnects the pump from the power source when the vacuum is greater than a predetermined pressure, for example greater than 0.6 bar.

Urine is drawn into the container through a tube 6 which goes into the top of the lid 11. The tube has a bore of 4–6 mm in this example. To minimize the tube's resistance to flow the bore needs to be large. However, an over-large bore causes the liquid column to break up when flowing uphill. The tubing needs to be crush resistant but in this version of the device, the valve 8 is a pinch valve and requires a flexible tube to act upon. Therefore the tube has a molded pliable insert 7 to be acted on by the pinch valve. This means that the tube can be disposed of without contaminating the valve with urine.

The electronic trigger can be any sort of device which is capable of rapidly detecting the presence of urine, e.g, a heat transducer, or an optical, resistance, or conductivity device. The manual trigger can be an electrical switch. Both the large and small container systems can use any of the triggers.

Figure 1A:
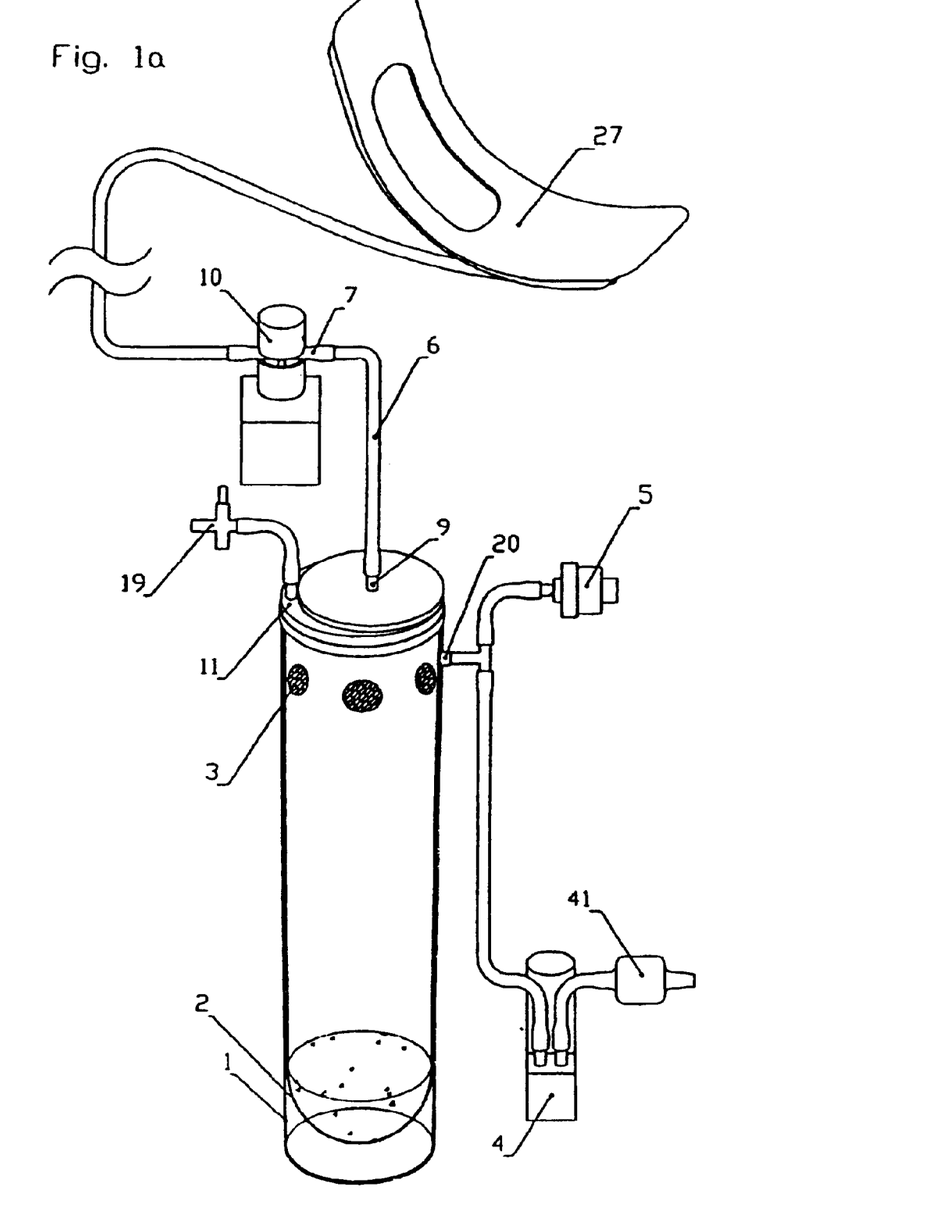
FIG. 1a shows an embodiment of large capacity device system with flat disc filter.
Figure 1B:
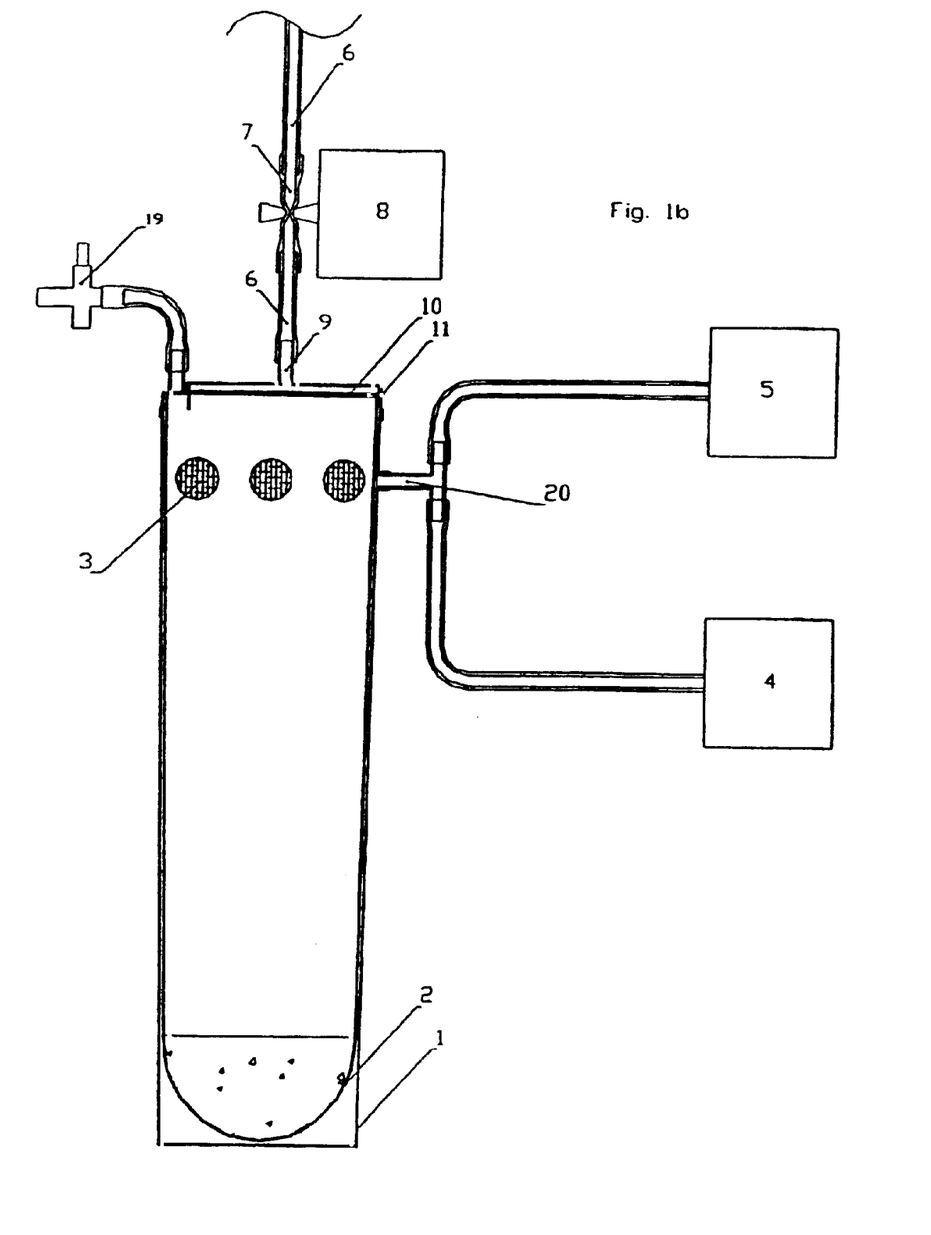
FIG. 1b is a cross-sectional view of the large capacity device with a flat disc filter.
Figure 1C:
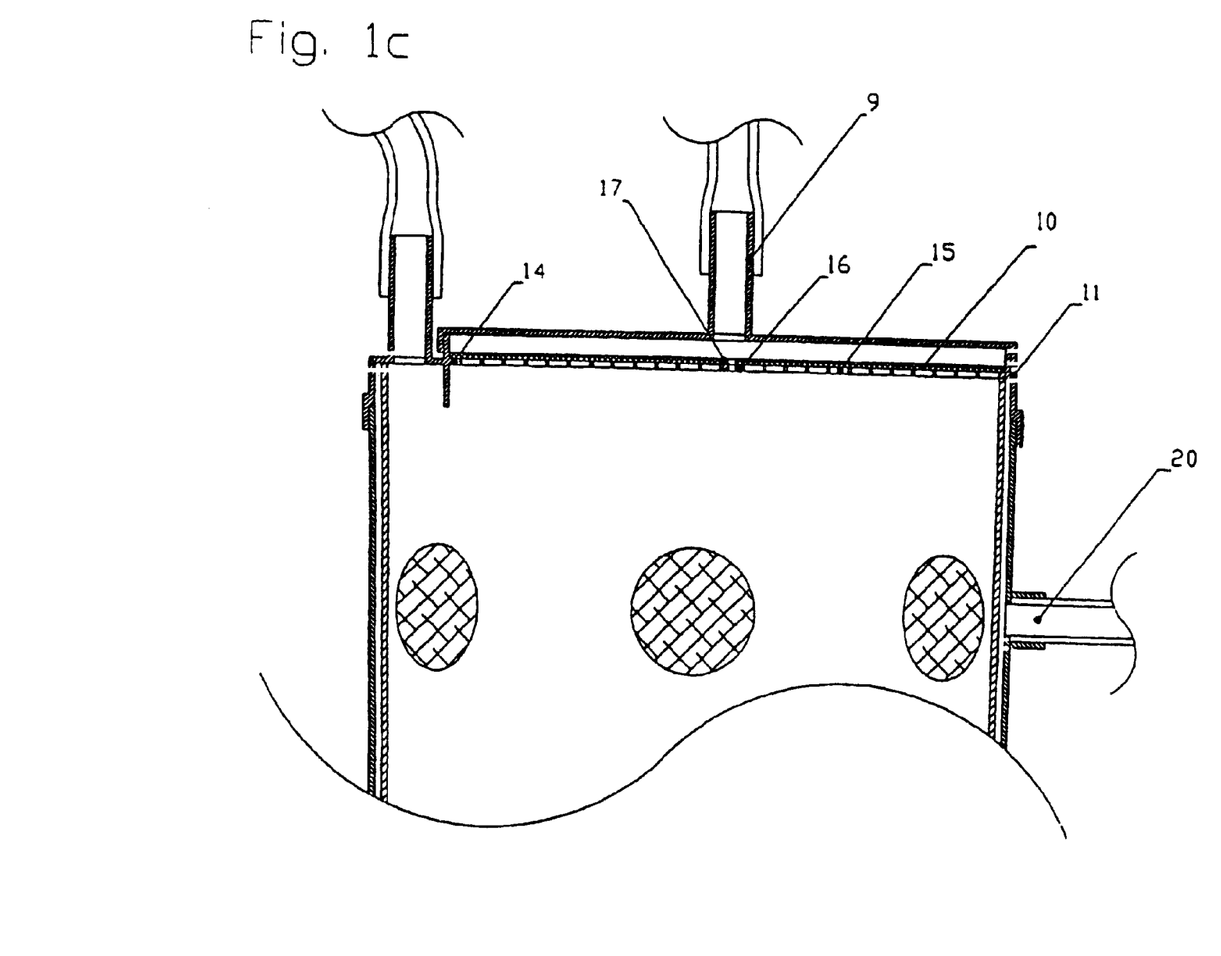
FIG. 1c is an enlarged cross-sectional view of top of the large capacity device with a flat disc filter.
Figure 2A:
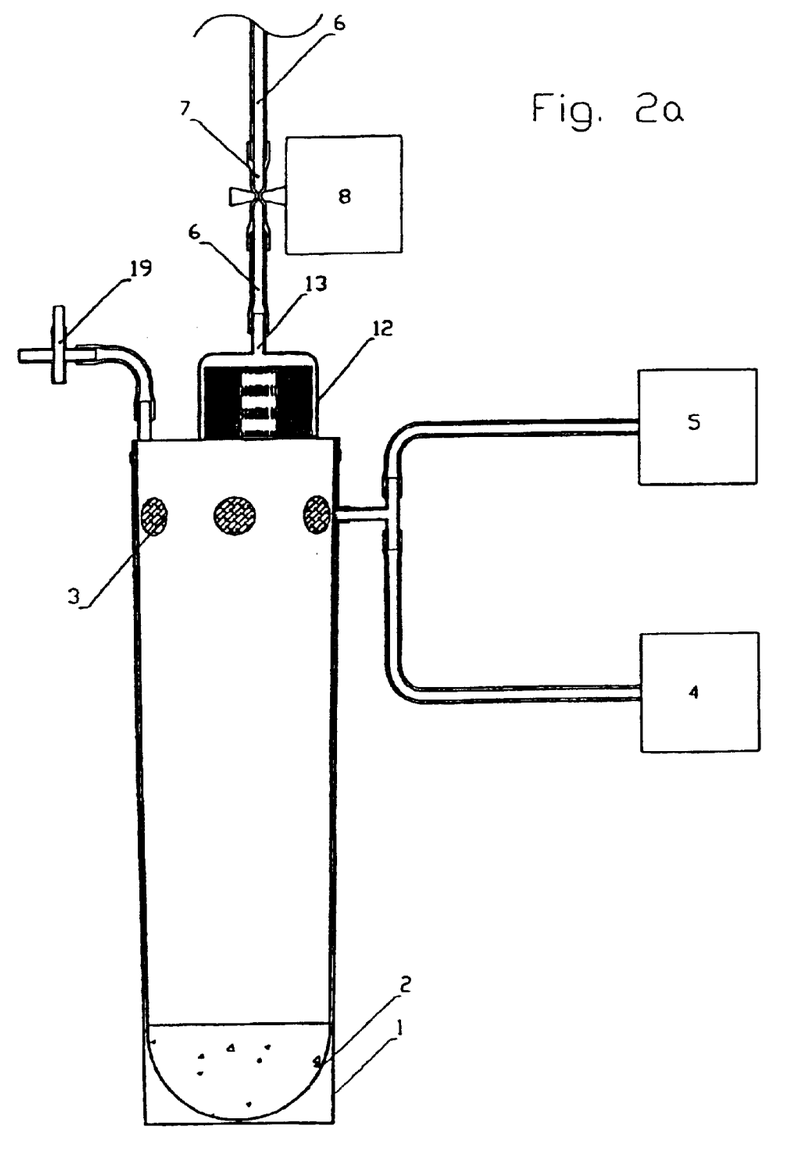
FIG. 2a is a cross-sectional view of an alternative embodiment of a large capacity device with cartridge filter.
Figure 2B:
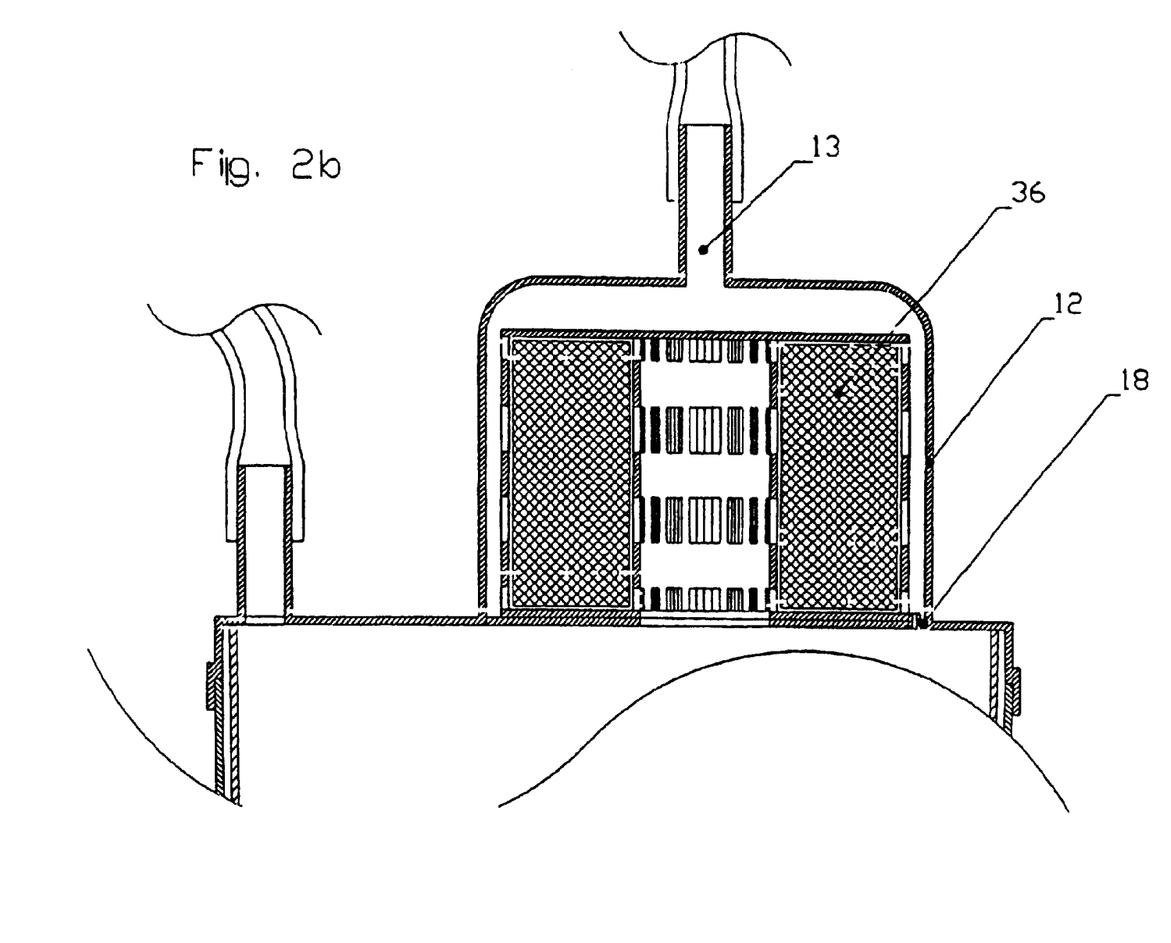
Figure 3A:
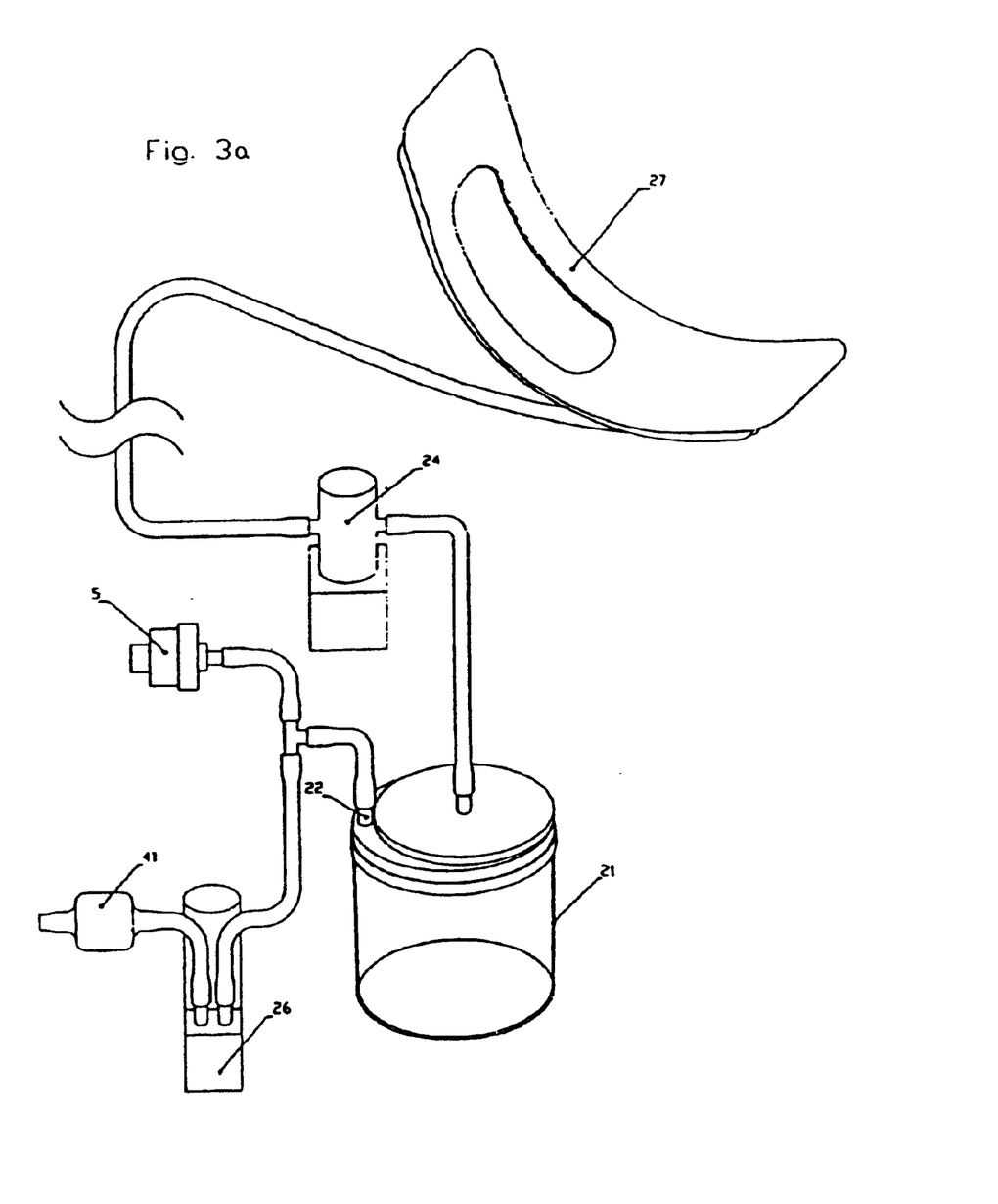
FIG. 3a shows an embodiment of complete small capacity device.
Figure 3B:
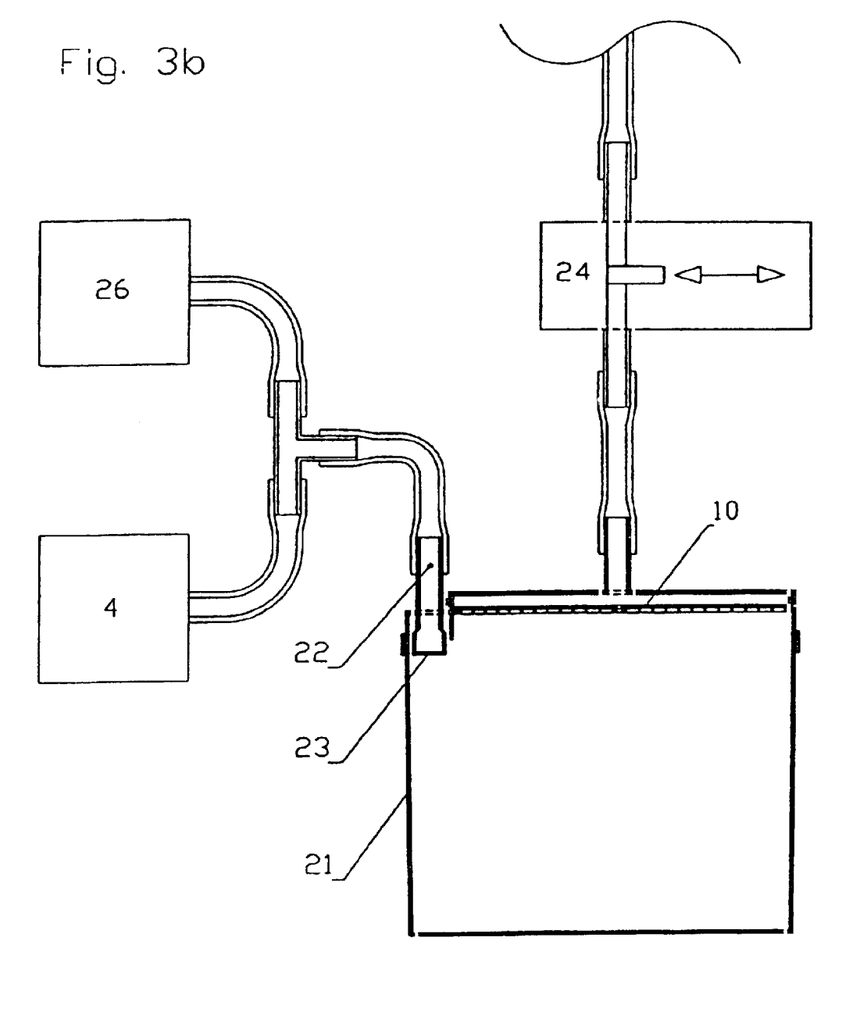
Figure 3C:
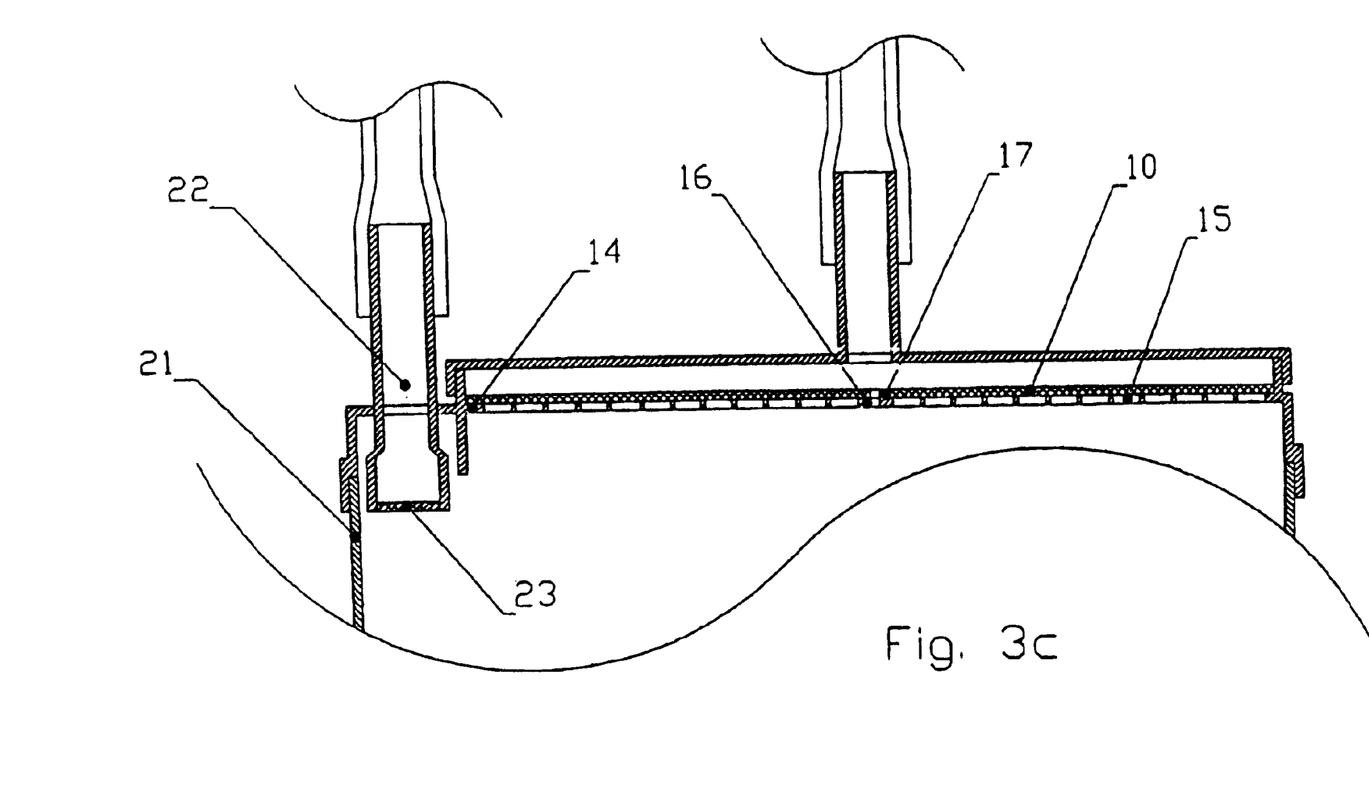

In FIGS. 1a, 1b, 1c and 3a, 3b, 3c the tubing will take urine from the interface to the inlet at the top of the lid of the container. The urine then passes through a filter material, in the lid of the container. In FIG. 2a the tubing will conduct the urine directly into the top of the filter cartridge housing 12 through inlet 13. This material has the effect of preserving the stored vacuum in the container by preferentially allowing aqueous liquid to pass through while resisting the passage of air/gas. The filter material could be a cellulose ester membrane filter with a defined pore size between 0.8 and 8 micrometers in this example. The filter may be a flat disc 10 incorporated in the lid of the storage container 11 or a filter cartridge 36 within a filter housing 12, incorporating 0.1–0.5 square meter effective filtration area. The flat disc filter 10 shown in FIGS. 1c and 3c is supported by a rigid disc of material 14 integral with the lid which is perforated. This section might also be made from a rigid wire or plastic mesh. Once the filter has been wetted it is impervious to air at the maximum pressure which the suction source can exert. It is therefore necessary both to remove the airlock and to allow the vacuum to reach the solenoid valve and ultimately the interface, to include a by-pass. For the flat disc filter a hole 17 0.1 mm–1 mm in diameter allows the removal of the air block at the beginning of second and subsequent urine flows. The filter will still allow liquid rather than air to pass when a mixed stream is drawn through the apparatus. For the filter cartridge, a capillary tube 18 by-pass from the base of the filter cartridge into the top of the storage container performs the same function as the hole 17 in the flat disc. These by-pass devices are positioned so that any liquid in the system will obstruct air flow through them.

Alternatively the by-pass hole could be in the filter support with a larger, non-critical size hole in the filter material.

In one embodiment, at the end of urination, when the system is empty, air will begin to flow through the filter by-pass causing the vacuum in the system to be lost, until the pressure transducer senses that the vacuum has fallen to 0.9 bar and causes and electronic control to switch the solenoid valve shut. Alternatively, the valve may be triggered to close and the pump operated to re-evacuate the storage container.

The large storage container system (FIGS. 1a, 1b, 2a, and 2b) preferably has sufficient capacity to store twelve hours urine production. When the bag is full, it can be emptied via the tap 19 in this diagram situated on one side of the lid. These systems will be most useful to wheelchair-bound individuals who can have the storage and pumping system behind or under the wheelchair. The preferred system would be the flat disc filter system because it is smaller and less expensive to produce. However, for elderly or ill people with a high level of urinary inclusions, the filter cartridge, with large effective filtration area, will be necessary to prevent blocking the filter prematurely.

The small capacity device of FIGS. 3a, 3b, 3c has a 300–600 ml capacity rigid storage container 21. In one embodiment there is no lining to the container. The container is evacuated through a tube in the lid 22 which is protected by a hydrophobic filter 23. The hydrophobic filter is to the same specifications as the filters in the wall of the liner in the large version of the device. In another embodiment, the small capacity device uses a liner with hydrophobic filters inset similar to the large capacity devices. This system is emptied after each void by removing the lid completely and pouring the contents away.

The solenoid valve 24 in this example is plugged in line to the tubing rather than acting on a molded section of the tube. The reason for this is that the plugged in solenoid valve is considerably lighter than the solenoid pinch valve.

This system is suitable for ambulant persons who could carry the device in a bag around the waist. It could also be useful to those wheelchair bound individuals who have good upper body mobility, but may not wish to be burdened with the more cumbersome large container system.

This small container system would also be beneficially used in conjunction with a urinal. The urinal and device could easily be stored in a small shoulder bag. The device and urinal could be flushed by pouring some mild disinfectant solution into the urinal after each use.

Figure 4:
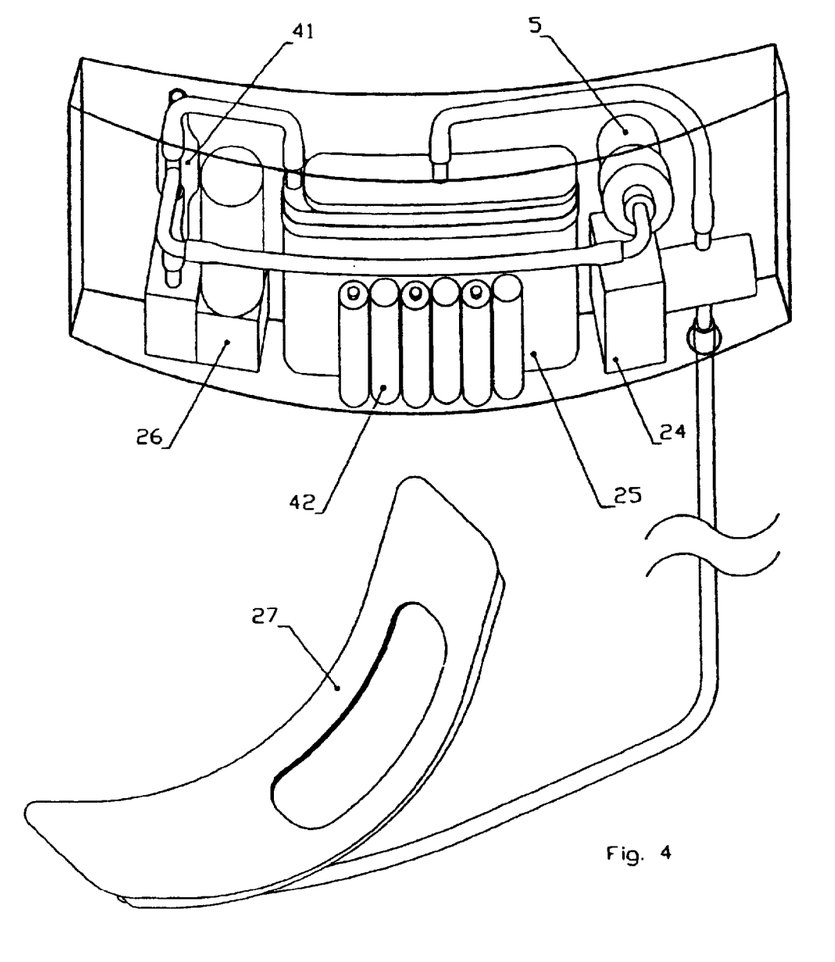
FIG. 4 shows another embodiment of a small capacity device system with ovoid storage container to fit in waist worn bag.

FIG. 4 shows the small capacity system fitted into a waist worn bag. In this illustration the cylindrical container has been replaced by an ovoid container 25 to give the whole system a neater and more comfortable fit. A lighter pump 26 may be used for this system and could be powered by six 1.5 volt AA size batteries 42. Any suitable battery pack or energy storage device could be used to power the pump 26.

The pumping and storage systems can be used with any of the different patient/device interfaces described below.

A reasonable space is preferably provided between the filter and the lid to prevent fluid from becoming trapped between the two surfaces, which could dramatically reduce flow rates.

A double lumen tube is preferably used to protect the sensor cable.

There may also be provided sound-proofing for the system.

Either a male urinal or a female urinal can be attached to the pumping and storage systems. The valve could be controlled by an electronic sensing device or more simply switched manually by the user as required.

Figure 5A:
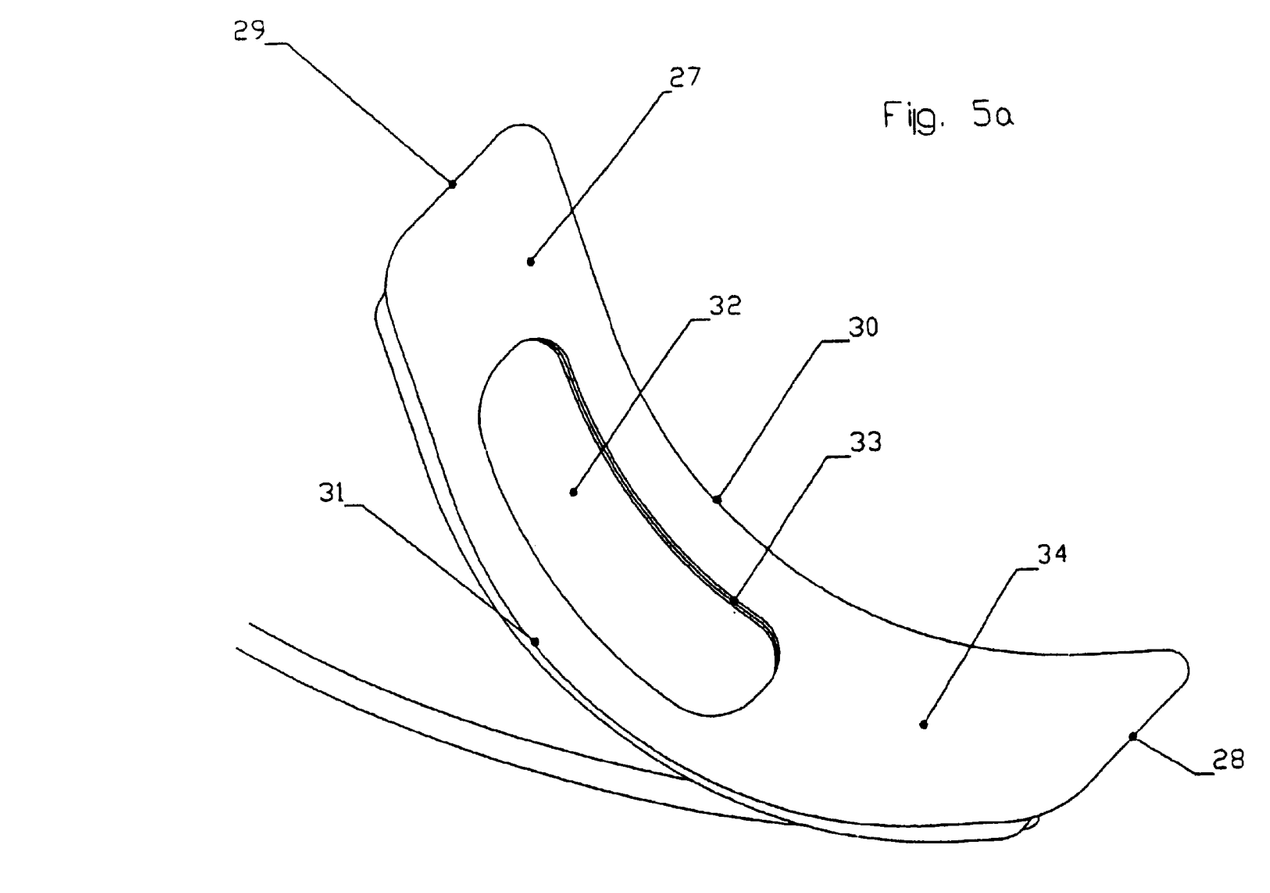
FIG. 5a shows an example of a layered female interface.
Figure 5B:
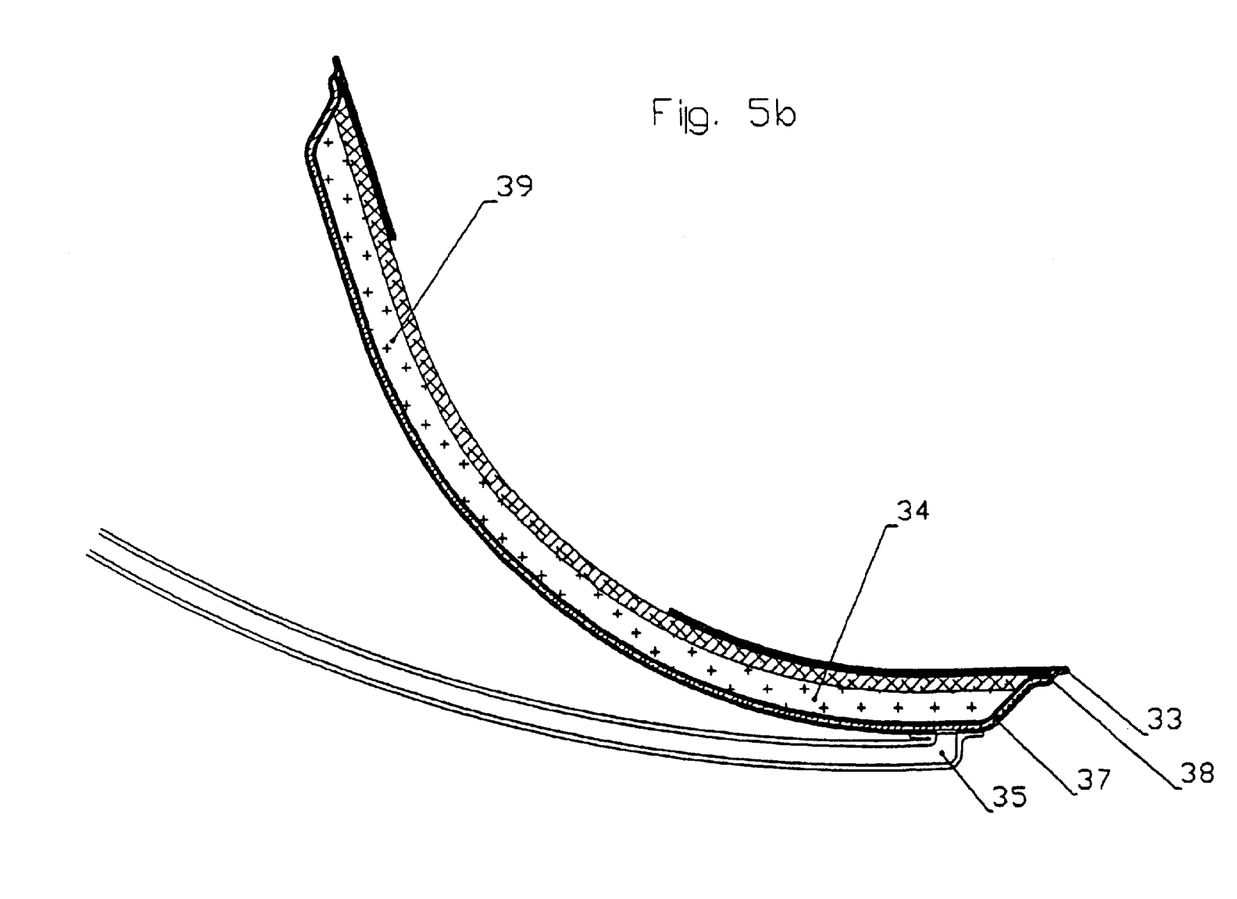

An embodiment of layered female interface 27 is shown in FIG. 5a and in detailed cross-section in FIG. 5b. The layered interface is generally curved rectangular in shape, having a lower edge 28, an upper edge 29 and side edges 30 and 31. The upper and lower edges may be straight as shown or rounded. The lower edge 28 is positioned towards the back of the person when worn and hence the upper edge 29 is towards the front. The rectangle is preferably only 5–9 cm wide, so that no bunching occurs in use, and 15–25 cm in length. The layered interface is curved in longitudinal cross-section to ensure a close fit to the body. There is a rounded rectangular hole 32 between 2–5 cm wide and 5–12 cm long, in the outer layer 33 of the interface. The hole is positioned towards the upper edge of the layered interface to correspond approximately with the urethral opening. This hole allows urine to penetrate rapidly into the layered interface and the covered section at the lower end of the layered interface provides a small reservoir 34 from which urine is sucked away. The suction tube is attached to the under surface of the layered interface at the lower end. The connector 35 penetrates the outer impervious layer 35 of the interface to communicate with the layer above 37.

The outer layer 33 of the layered interface is impervious to air and liquids. It may be made of any suitable material, for example polyethylene or polypropylene sheets or nonwoven materials coated with latex or silicone. Immediately above the impervious layer there is a spacing layer 37 composed of open-surfaced material that allows aqueous liquid to flow between layer 33 and 38 without restricting the flow. Polyester wadding, fibrous material, open celled foam or similar materials could be used to form this layer. Layer 38 is a nylon mesh, with 3–10 mm pore size which is bonded in the pad so that the urine has to pass through it before passing through the suction tube. This mesh preferentially allows liquid to flow through while slowing the passage of air and is used to avoid the loud sucking noise which otherwise occurs at rapid rates of air/urine uptake. Above the nylon mesh there is a layer of open-structured shape-retaining material 39. This layer provides structural stability and allows urine to flow down the length of the interface into the reservoir section 34 at the lower end. The layer above is a receiving layer 40 which rapidly takes up urine and allows it to flow through to the lower layers. This could be a polyester fleece, needle-felt or any suitable soft comfortable material. An additional cover-stock layer may be added to cover the patient contact surface which would help to reduce wet-back and increase patient comfort. The entire layered interface will need to be positioned within specially designed underwear.

The invention is not intended to be limited to the preferred versions described above, but rather is intended to be limited only by the claims set out below. Thus, the invention encompasses all alternate versions that fall literally or equivalently within the scope of these claims.

What is claimed is:

1. A urine collection device for collecting urine produced by a person, comprising:
   a. a container for storing collected urine;
   b. an interface for collecting urine from the urethral opening of a user;
   c. a valve operable to open communication between the interface and the container;
   d. a pump operable to produce a vacuum within the container;
   e. a vacuum sensor coupled to the pump for maintaining the vacuum substantially continuously during use of the device, including during intermittent operation of the valve;
   f. a urine sensor operable to sense the presence of urine at the interface and to operate the valve to open communication between the interface and the container to cause said vacuum to draw urine from the interface to the container.

2. The urine collection device of claim 1 further comprising a filter at or adjacent the top of said container allowing egress of urine or other aqueous fluids, but at least substantially preventing egress of air into the container.

3. The urine collection device of claim 1 further comprising a filter in the container allowing egress of air from drawn urine but substantially preventing egress of urine or other fluids.

4. The urine collection device of claim 3 wherein the filter at least substantially prevents egress of bacteria from said container.

5. The urine collection device of claim 1 wherein the urine sensor includes a heat transducer.

6. The urine collection device of claim 1 wherein the urine sensor includes an optical sensor.

7. The urine collection device of claim 1 wherein the urine sensor includes a resistivity sensor.

8. The urine collection device of claim 1 wherein the urine sensor includes a conductivity sensor.

9. A method of collecting urine in a collection device, the collection device including
   (i) a container for storing collected urine,
   (ii) a urethral tract opening interface,
   (iii) a pump operable to create a vacuum in the container, and
   (iv) a valve operable to open communication between the interface and the container, the method including the steps of:
   a. providing a substantially continuous vacuum in said container,
   b. maintaining the vacuum including on intermittent operation of the valve,
   c. sensing the presence of urine at the interface, and
   d. opening communication from the interface to the container on sensing of urine at the interface.

10. A method according to claim 9 wherein urine is drawn at the rate at which it is produced.

11. A method according to claim 10 wherein urine is drawn at a predetermined rate equivalent to the expected rate of production of urine.

12. A urine collection device comprising:
   a. an interface having an interface interior wherein urine is collected from the urethral opening of a user;
   b. a container downstream from the interface, the container having a container interior wherein urine is collected from the interface, and wherein the container interior is continuously maintained at lower pressure than the interface interior;
   c. a valve situated between the interface and the container, the valve being operable to allow fluid communication between the interface and the container;
   d. a urine sensor operable to detect the presence of urine upstream from the valve, the urine sensor communicating with the valve,
   wherein the urine sensor opens the valve upon detection of urine, thereby allowing the lower pressure within the container interior to draw urine from the interface into the container.

13. The urine collection device of claim 12 further comprising a filter interposed between the interface and the container.

14. The urine collection device of claim 12 further comprising a liner situated within the container, with the container interior being situated within the liner.

15. The urine collection device of claim 14 wherein the container is foraminated, thereby maintaining any space between the container and liner at ambient pressure.

16. The urine collection device of claim 12 wherein the interface interior is occupied by porous material.

17. The urine collection device of claim 16 wherein the interface is defined by a pad contoured to fit the human body, and wherein the pad has one or more apertures defined therein to allow passage of urine to the porous material.

18. The urine collection device of claim 12 wherein the urine sensor includes at least one of:
   a. a heat sensor;
   b. a resistivity sensor; and
   c. a conductivity sensor.

* * * * *